US010148282B1

United States Patent
Govari et al.

(10) Patent No.: US 10,148,282 B1
(45) Date of Patent: Dec. 4, 2018

(54) HETERODYNE-MIMICKING ADAPTER

(71) Applicant: BIOSENSE WEBSTER (ISRAEL) LTD., Yokneam (IL)

(72) Inventors: Assaf Govari, Haifa (IL); Vadim Gliner, Haifa (IL)

(73) Assignee: Biosense Webster (Israel) Ltd. (IL)

(*) Notice: Subject to any disclaimer, the term of this patent is extended or adjusted under 35 U.S.C. 154(b) by 0 days.

(21) Appl. No.: 15/689,677

(22) Filed: Aug. 29, 2017

(51) Int. Cl.
*A61B 18/14* (2006.01)
*H03M 3/00* (2006.01)
*A61B 18/00* (2006.01)

(52) U.S. Cl.
CPC .............. *H03M 3/41* (2013.01); *A61B 18/14* (2013.01); *H03M 3/352* (2013.01); *H03M 3/39* (2013.01); *H03M 3/496* (2013.01); *A61B 2018/00351* (2013.01); *A61B 2018/00577* (2013.01)

(58) Field of Classification Search
CPC .................. A61B 18/14; A61B 5/0538; A61B 2017/00477; A61B 2018/00178; A61B 2017/00486; A61B 2017/00017; A61B 5/01; A61B 5/021; A61B 7/00; A61B 18/1492; A61B 5/0422; A61B 5/0816; A61B 5/685; A61B 2017/0003; A61B 2018/1467
USPC .......... 455/314, 575.1, 557, 423–425, 67.11; 600/300, 522, 386; 340/539.12
See application file for complete search history.

(56) References Cited

U.S. PATENT DOCUMENTS

| | | | |
|---|---|---|---|
| 4,471,399 A | 9/1984 | Udren | |
| 6,373,422 B1 | 4/2002 | Mostafa | |
| 7,860,189 B2 | 12/2010 | Petilli et al. | |
| 2002/0197989 A1 | 12/2002 | Cruder et al. | |
| 2006/0114986 A1* | 6/2006 | Knapp, II | A61B 1/00103 375/240.01 |
| 2013/0131755 A1 | 5/2013 | Panken et al. | |

* cited by examiner

*Primary Examiner* — Keith Ferguson
(74) *Attorney, Agent, or Firm* — Vincent J. Serrao

(57) ABSTRACT

An adapter, for coupling a first medical instrument to a control console having a console receptacle configured for attachment thereto of a different second medical instrument, includes a case, a receptacle, circuitry contained in the case and an output connector. The receptacle is configured to receive an input connector of the first medical instrument conveying modulated analog input signals from the first medical instrument. The circuitry includes an analog/digital converter coupled to sample and digitize the analog input signals to generate digital samples, digital processing circuitry configured to digitally downconvert the digital samples so as to generate a baseband digital signal, and a digital/analog converter configured to convert the baseband digital signal to an analog baseband signal compatible with an output of the second medical instrument. The output connector is configured to be inserted into the console receptacle and to convey the analog baseband signal to the console.

9 Claims, 2 Drawing Sheets

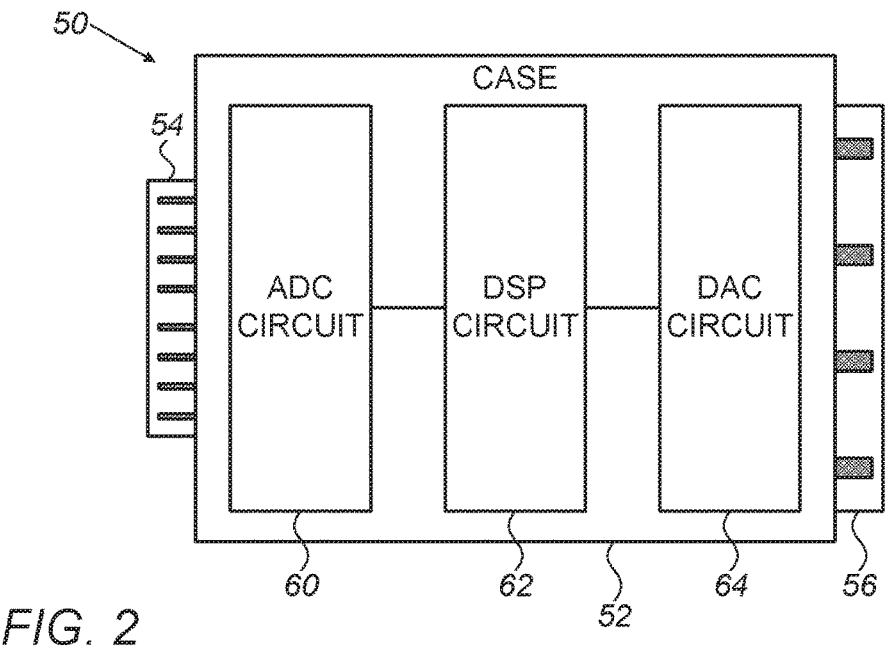
FIG. 2
FIG. 3
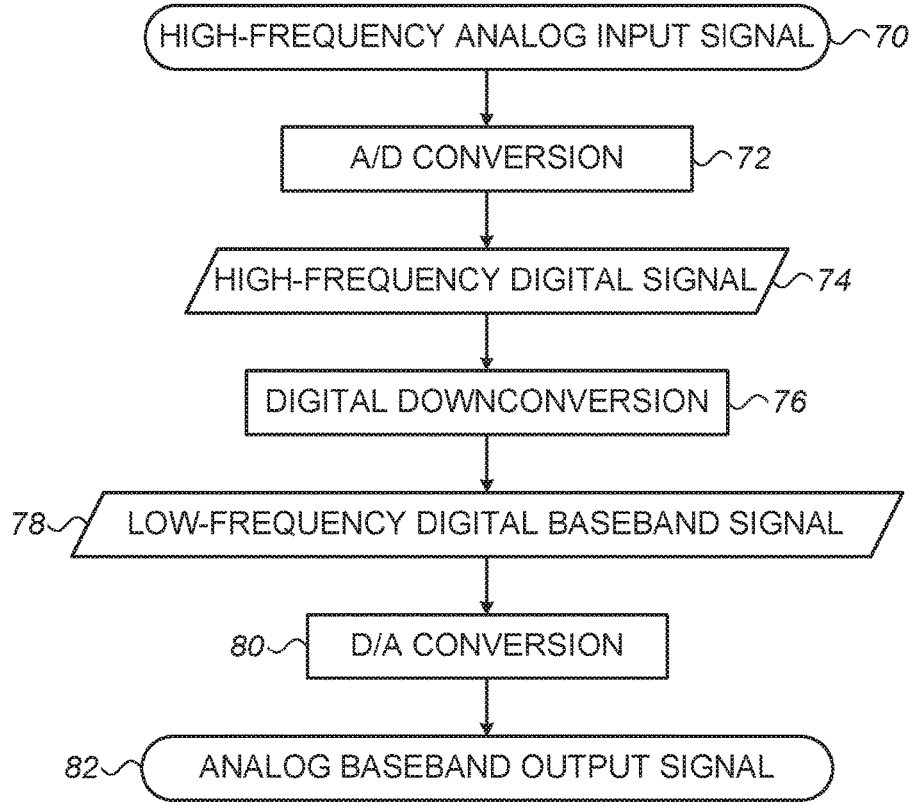

HETERODYNE-MIMICKING ADAPTER

FIELD OF THE INVENTION

The present invention relates generally to apparatus and methods for signal-processing in medical instruments, and particularly to adapters for transferring signals acquired by probes to a control console.

BACKGROUND OF THE INVENTION

Heterodyning is a well-established signal processing technique. For example, U.S. Pat. No. 7,860,189 describes hybrid heterodyne transmitters and receivers for use in communications systems, or other systems, and the corresponding methods for hybrid heterodyne transmitting and receiving. A heterodyne receiver for converting a continuous time modulated signal to a discrete time digital baseband signal includes receiving a modulated signal at an RF carrier frequency and provide a quantized output at an intermediate frequency. The digital mixer then provides digital signals representative of a baseband signal suitable for digital signal processing.

As another example, U.S. Pat. No. 6,373,422 describes a radio frequency signal received by an analog-to-digital converter in order to convert the signal from an analog signal into a digital signal. The digital signal is then provided to a decimation filter in order to convert the digital signal into a base band signal. By using a decimation filter the need for a second down conversion mixer is eliminated, thereby eliminating any associated noise, power consumption and distortion associated with using a second mixer.

As yet another example, US Patent Application Publication 2013/0131755 describes a heterodyning architecture applied to convert a selected frequency band of a physiological signal to a baseband for analysis. As an example, the baseband components of the signal may have a frequency in the range of hundreds of Hertz and the carrier frequency is in the range of several kHz. The original baseband components of the signal are chopped to a higher frequency band, e.g., several kHz. Thus, the low-frequency noise signal is segregated from the original baseband components of the signal.

SUMMARY OF THE INVENTION

An embodiment of the present invention provides an adapter for coupling a first medical instrument to a control console having a console receptacle configured for attachment thereto of a different, second medical instrument. The adapter includes a case, a receptacle on the case, circuitry contained in the case, and an output connector on the case. The receptacle on the case is configured to receive an input connector of the first medical instrument conveying modulated analog input signals from the first medical instrument. The circuitry contained in the case includes an analog/digital converter (ADC), which is coupled to sample and digitize the analog input signals to generate a stream of digital samples, digital processing circuitry, which is configured to digitally downconvert the stream of digital samples so as to generate a baseband digital signal, and a digital/analog converter (DAC), which is configured to convert the baseband digital signal to an analog baseband signal compatible with an output of the second medical instrument. The output connector on the case is configured to be inserted into the console receptacle and to convey the analog baseband signal to the console.

In some embodiments, the analog input signals are modulated onto different carrier frequencies, and the circuitry is configured to convert the analog input signals into multiple baseband signals having different baseband frequencies. In an embodiment, the ADC, the digital processing circuitry and the DAC are integrated on a single circuit board. In some embodiments, the receptacle is configured to receive the analog input signals from one or more contact-force sensors fitted to the distal end of a medical instrument. In another embodiment, the control console is part of a catheter-based ablation system.

There is additionally provided, in accordance with an embodiment of the present invention, a method for coupling a first medical instrument to a control console configured for attachment thereto of a different, second medical instrument. The method includes, in an adapter, receiving modulated analog input signals from the first medical instrument. Circuitry in the adapter is used for sampling and digitizing the analog input signals to generate a stream of digital samples, digitally downconverting the stream of digital samples so as to generate a baseband digital signal, and converting the baseband digital signal to an analog baseband signal compatible with an output of the second medical instrument. The analog baseband signal is conveyed from the adapter to the console.

The present invention will be more fully understood from the following detailed description of the embodiments thereof, taken together with the drawings in which:

BRIEF DESCRIPTION OF THE DRAWINGS

FIG. 2 is a block diagram that schematically illustrates a heterodyne-mimicking adapter, in accordance with an embodiment of the present invention; and FIG. 3 is a flow chart that schematically illustrates a method for signal processing in a heterodyne-mimicking adapter, in accordance with an embodiment of the present invention.

DETAILED DESCRIPTION OF EMBODIMENTS

Overview

Figure 1:
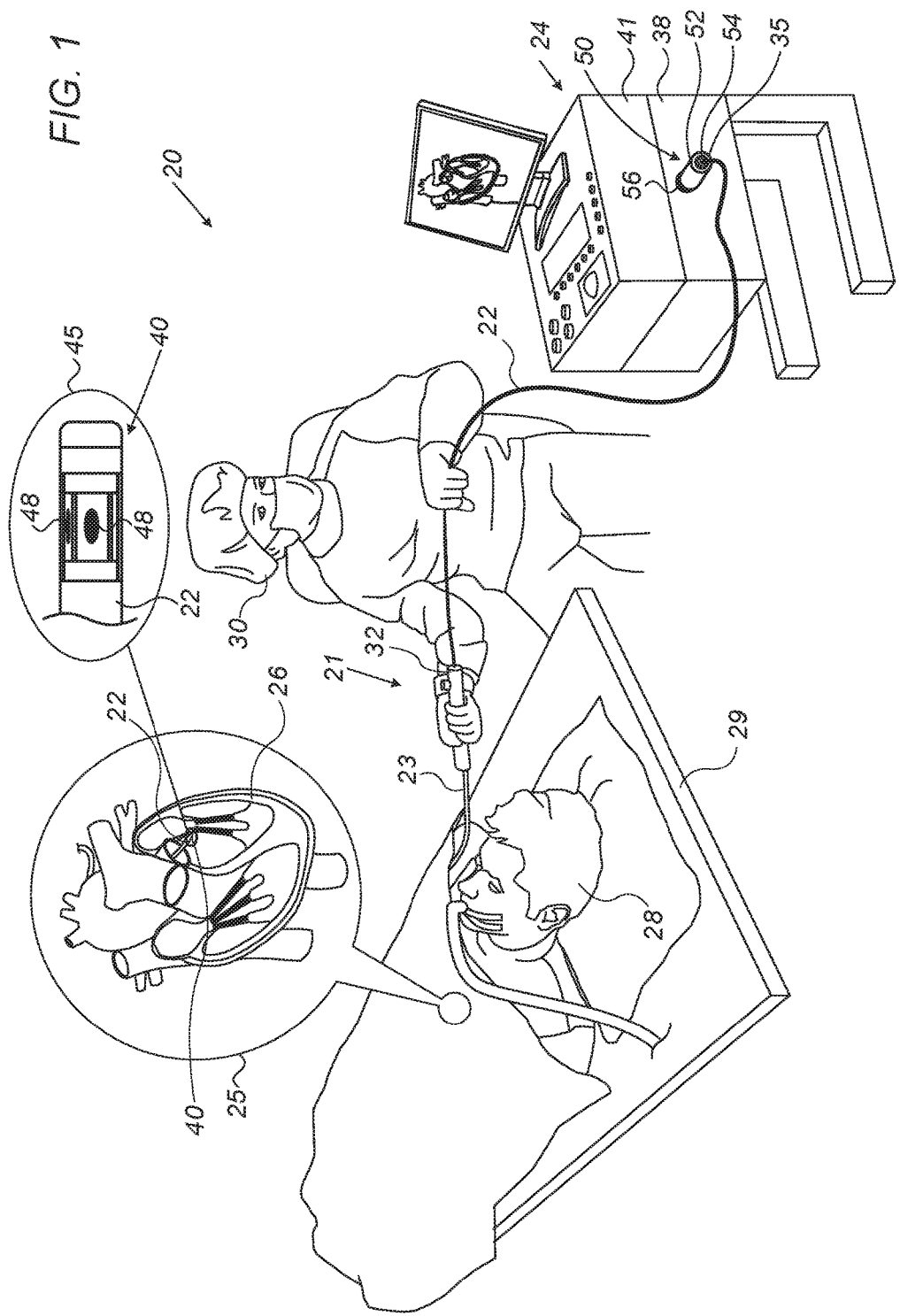
FIG. 1 is a schematic, pictorial illustration of a catheter-based ablation system equipped with a heterodyne-mimicking adapter, in accordance with an embodiment of the present invention.

Sensors fitted in medical instruments, such as catheters, typically generate multiple different analog signals. For example, contact-force sensors in legacy ablation catheters are often configured to generate relatively low-frequency analog signals, whereas sensors of newer ablation catheters often generate higher-frequency signals. Heterodyning is commonly applied for extracting baseband content from relatively low-frequency signals, before further transmitting the information to the system's console. Some of the new medical devices, however, transmit very high frequencies, in which case heterodyning may cause signal corruption, as explained below.

Embodiments of the present invention that are described herein provide an adapter for medical instruments that can perform heterodyne-like extraction of an analog baseband signal from analog signals comprising high frequencies. The disclosed heterodyne-mimicking adapter comprises circuitry that digitally samples the high-frequency analog signal, then digitally downconverts the samples to generate a digital baseband signal, and then converts the digital baseband signal back into an analog baseband signal compatible with the baseband signal that the legacy system consoles receive from legacy medical instruments.

In some embodiments, the circuitry is contained in an adapter connected between the medical instrument cabling and the medical instrument console. The adapter comprises a receptacle that accepts new medical instrument designs which require such an adapter in order to operate with legacy system consoles, and an output connector that fits the receptacle of the legacy consoles. Thus, the legacy system console is able to function with, for example, new high-frequency contact-force sensors fitted at the distal end of a catheter, without any changes.

In some embodiments, the circuitry in the adapter case comprises a high-frequency analog-to-digital converter (ADC) coupled to the input receptacle, digital signal processing (DSP) circuitry, and a low-frequency digital-to-analog converter (DAC) coupled to the output plug. The ADC digitizes the high-frequency signals received from the medical instrument. The DSP circuitry downconverts the digitized signals to baseband. The DAC converts the baseband signals into a low-frequency analog signal that is provided to the legacy console.

The disclosed heterodyne-mimicking adapter has a distinct advantage over analog heterodyne solutions attempting to perform similar function, in that it does not corrupt the baseband signal. This performance becomes especially significant when the signal frequency is high. In such cases, the corruption of the baseband signal by the analog heterodyne solutions may render such solutions impractical.

System Description

FIG. 1 is a schematic, pictorial illustration of a catheter-based ablation system 20 equipped with a heterodyne-mimicking adapter, in accordance with an embodiment of the present invention. System 20 comprises a catheter 21, having an insertion-tube 22 that is navigated by a physician 30 into a heart 26 of a patient 28 lying on a table 29. In the pictured example, physician 30 inserts insertion-tube 22 through a sheath 23, while manipulating insertion-tube 22 using a manipulator 32 near the proximal end of the catheter.

As shown in an inset 25, insertion-tube 22 comprises a device 40 fitted at its distal end, which requires a heterodyne-mimicking adapter 50 in order to connect and operate with system 20. An inset 45 shows an arrangement of high-frequency contact force sensors 48 within device 40. Sensors 48 generate signals comprising a slowly modulated amplitude of a high-frequency carrier-wave. For example, the amplitude of the carrier-wave may be modulated at a modulation rate of 100 Hz, while the carrier frequency itself is on the order of 100 KHz. Alternatively, however, any other suitable modulation rates and carrier frequencies can be used.

Analog heterodyning techniques, such as the techniques used with legacy medical instruments, are inferior in processing modulation frequencies which are many orders of magnitude below the carrier frequencies. One reason is that the analog amplifiers themselves introduce stray-signals at frequencies that fall within the baseband frequencies, and since analog amplifiers also convert frequency-drifts of the carrier-wave itself into stray-signal frequencies that fall within the baseband frequencies as well. All of these stray signals corrupt the baseband signal.

High-frequency signals, which the heterodyne-mimicking adapter is configured to convert into baseband signals, may originate from any other kind of high-frequency sensor, not necessarily the contact-force sensors shown in FIG. 1. Moreover, such signals may originate from altogether other kinds of high-frequency sources contained in medical instruments.

In the embodiment described herein, catheter 21 may be used for any suitable therapeutic and/or diagnostic purposes, such as ablation of tissue in a heart 26.

As seen in the figure, the proximal end of catheter is connected by its built-in connector 35 to a heterodyne-mimicking adapter 50 via a receptacle 54, where receptacle 54 is configured for that purpose. Adapter 50 is further connected to a control console 24 with an output connector 56, which is part of adapter 50 and is configured for that purpose. Control console 24 comprises a processor 41, typically a general-purpose computer, with suitable front end and interface circuits 38 for receiving signals from catheter 21, as well as for applying energy via catheter 21 to ablate tissue in heart 26 and for controlling the other components of system 20.

Processor 41 is typically programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

Heterodyne-Mimicking Adapter Description

FIG. 2 is a block diagram that schematically illustrates adapter 50, in accordance with an embodiment of the present invention. As seen from the outside, adapter 50 comprises a case 52, a receptacle 54 and an output connector 56. Inside the case, adapter 50 comprises a high-frequency analog-to-digital converter (ADC) circuit 60, a digital signal processing (DSP) circuit 62, and a low-frequency digital-to-analog converter (DAC) circuit 64. In the present context, ADC circuit 60, DSP circuit 62 and DAC circuit 64 are referred to collectively as "circuitry" that carries out the digital processing functions of the adapter.

In the example of FIG. 2, a single high-speed ADC digitizes the plurality of signals received from sensors 48. In an alternative embodiment, adapter 50 may comprise two or more ADCs, each configured to digitize a respective subset of the received signals. By the same token, in the example of FIG. 2 a single DAC converts the plurality of baseband signals to analog signals. In an alternative embodiment, adapter 50 may comprise two or more DACs, each configured to convert a respective subset of the baseband signals.

In an embodiment, ADC 60, DSP 62 and DAC 64 are all integrated on a single printed circuit board. The various elements of adapter 50 may be implemented in hardware, e.g., using one or more discrete components, Field-Programmable Gate Arrays (FPGAs) or Application-Specific Integrated Circuits (ASICs). In some embodiments, some elements of adapter 50, e.g., DSP 62, may be implemented in software, or using a combination of software and hardware elements. The configuration of adapter 50 shown in FIG. 2 is an example configuration, which is depicted purely for the sake of conceptual clarity. In alternative embodiments, adapter 50 may be implemented using any other suitable components or configuration.

FIG. 3 is a flow chart that schematically illustrates a method for signal processing in heterodyne-mimicking adapter 50, in accordance with an embodiment of the present invention. As seen, a high-frequency analog input signal 70 is converted into a high-frequency digital signal 74 comprising a stream of digital samples, by ADC circuit 60, at an A/D conversion step 72. The stream of digital samples is further digitally downconverted into a low-frequency digital baseband signal 78, by DSP circuit 62, at a downconverting step 76. The digital baseband signal is then converted back into an analog baseband output signal 82, by DAC circuit 64, at a D/A conversion step 80.

As described above, in some embodiments, the control console has a console receptacle configured for attachment of legacy medical instruments. Such legacy medical instruments typically generate signals comprising lower frequencies compared with the new medical instruments, for example comprising a carrier-frequency of only 10 KHz vs. the 100 Khz carrier-frequency exemplified above. When there is a need to attach to the control console a newer medical instrument via adapter 50, the adapter will provide output baseband analog signals that are compatible with the analog output baseband signals of the legacy medical instruments. Thus, the same console can now handle both signals originating from legacy medical instruments, such as legacy catheters, without the need in adapter 50, and signals from new high-frequency medical instruments, such as new catheters—with adapter 50.

The example configurations shown in the figures are chosen purely for the sake of conceptual clarity. In alternative embodiments, the disclosed techniques may use other suitable configurations comprising other medical instruments coupled by the disclosed adapter-plug receptacle, for example endoscopes, and other medical systems coupled by the adapter-plug connector, for example probe position sensing systems. The properties of signals, the architecture and functionality of the adapter may vary, such as for example the values of the high frequencies, the values of the baseband frequencies, and the number of signal channels/frequencies the adapter can convert in parallel.

In an example embodiment, the carrier frequencies of the high-frequency analog signals may be 16.75 kHz, and higher carrier frequencies, e.g., up to 60 kHz, may be selected. The signal bandwidth in this example embodiment is approximately 1 kHz, e.g., 1060 Hz. In other embodiments, however, the carrier frequencies of the high-frequency analog signals may be chosen in the range of 10-100 kHz.

The baseband analog signals may have bandwidths on the order of up to 5 kHz. Alternatively, any other suitable values can be used.

As another example, the adapter may be configured to analyze the baseband signals it generated as to derive measurements, such as a contact-force value.

Although the embodiments described herein mainly address medical sensors, the methods and systems described herein can also be used in any other suitable application that uses sensors, including various military applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An adapter for coupling a first medical instrument to a control console having a console receptacle configured for attachment thereto of a different, second medical instrument, the adapter comprising:
   a case;
   a receptacle on the case, which is configured to receive an input connector of the first medical instrument conveying modulated analog input signals from the first medical instrument;
   circuitry contained in the case, which comprises:
      an analog/digital converter (ADC), which is coupled to sample and digitize the analog input signals to generate a stream of digital samples;
      digital processing circuitry, which configured to digitally downconvert the stream of digital samples so as to generate a baseband digital signal; and
      a digital/analog converter (DAC), which is configured to convert the baseband digital signal to an analog baseband signal compatible with an output of the second medical instrument; and
   an output connector on the case, configured to be inserted into the console receptacle and to convey the analog baseband signal to the console.

2. The adapter according to claim 1, wherein the analog input signals are modulated onto different carrier frequencies, and wherein the circuitry is configured to convert the analog input signals into multiple baseband signals having different baseband frequencies.

3. The adapter according to claim 1, wherein the ADC, the digital processing circuitry and the DAC are integrated on a single circuit board.

4. The adapter according to claim 1, wherein the receptacle is configured to receive the analog input signals from one or more contact-force sensors fitted to the distal end of a medical instrument.

5. The adapter according to claim 1, wherein the control console is part of a catheter-based ablation system.

6. A method for coupling a first medical instrument to a control console configured for attachment thereto of a different, second medical instrument, the method comprising:
   in an adapter, receiving modulated analog input signals from the first medical instrument;
   using circuitry in the adapter:
      sampling and digitizing the analog input signals to generate a stream of digital samples;
      digitally downconverting the stream of digital samples so as to generate a baseband digital signal; and
      converting the baseband digital signal to an analog baseband signal compatible with an output of the second medical instrument; and
   conveying the analog baseband signal from the adapter to the console.

7. The method according to claim 6, wherein the analog input signals are modulated onto different carrier frequencies, and wherein converting the baseband digital signal to the analog baseband signal comprises converting the analog input signals into multiple baseband signals having different baseband frequencies.

8. The method according to claim 6, wherein receiving the analog input signals comprises receiving the analog input signals from one or more contact-force sensors fitted to the distal end of the first medical instrument.

9. The method according to claim 6, wherein the control console is part of a catheter-based ablation system.

* * * * *